United States Patent [19]

Johnson et al.

[11] Patent Number: 4,952,746
[45] Date of Patent: Aug. 28, 1990

[54] PROCESS FOR THE REMOVAL OF HYDROGENATABLE HYDROCARBONACEOUS COMPOUNDS FROM A HYDROCARBONACEOUS STREAM AND HYDROGENATING THESE COMPOUNDS

[75] Inventors: Russell W. Johnson, Elmhurst; Lee Hilfman, Mount Prospect, both of Ill.

[73] Assignee: UOP, Des Plaines, Ill.

[21] Appl. No.: 144,207

[22] Filed: Jan. 15, 1988

Related U.S. Application Data

[63] Continuation-in-part of Ser. No. 930,624, Nov. 14, 1986, abandoned.

[51] Int. Cl.$^5$ .................... C07C 7/13; C07C 7/11; C07C 7/12
[52] U.S. Cl. .................. 585/802; 208/210; 208/211; 208/212; 208/251 H; 208/254 H; 208/262.1; 208/262.5; 585/258; 585/823; 585/826
[58] Field of Search ............. 585/258, 251, 264, 802, 585/823, 826; 208/210, 211, 212, 251 H, 254 H, 262.1, 262.5

[56] References Cited

U.S. PATENT DOCUMENTS

| | | | |
|---|---|---|---|
| 3,595,931 | 7/1971 | Hay et al. | 260/668 |
| 3,892,818 | 7/1975 | Scharfe et al. | 260/676 |
| 3,919,398 | 11/1975 | Davis | 423/481 |
| 4,201,665 | 5/1980 | Savage et al. | 210/32 |
| 4,578,194 | 3/1986 | Reinartz et al. | 210/673 |

OTHER PUBLICATIONS

Kirk–Othmer, *Encyclopedia of Chemical Technology*, Third Edition, vol. 12, p. 999.

*Primary Examiner*—Asok Pal
*Attorney, Agent, or Firm*—Thomas K. McBride; John G. Tolomei; John G. Cutts, Jr.

[57] ABSTRACT

A process for the removal of hydrogenatable hydrocarbonaceous compounds comprising a component selected from the group consisting of halogen, metal, sulfur, oxygen and nitrogen from a hydrocarbonaceous stream which comprises the steps of: (a) contacting the hydrocarbonaceous stream with an adsorbent to remove at least a portion of the hydrogenatable hydrocarbonaceous compounds from the hydrocarbonaceous stream to provide a hydrocarbonaceous stream having a reduced concentration of hydrogenatable hydrocarbonaceous compounds; (b) contacting spent adsorbent with an elution solvent to remove the hydrogenatable hydrocarbonaceous compounds from the spent adsorbent thereby regenerating the adsorbent; (c) contacting the elution solvent in admixture with the hydrogenatable hydrocarbonaceous compounds in the presence of hydrogen with a hydrogenation catalyst; (d) contacting the effluent with an aqueous scrubbing solution; (e) introducing a resulting admixture of the reaction zone effluent and the aqueous scrubbing solution into a separation zone to provide a hydrotreated elution solvent and a spent aqueous stream; and (f) recycling at least a portion of the hydrotreated elution solvent from step (e) to provide at least a portion of the elution solvent utilized in step (b).

14 Claims, 1 Drawing Sheet

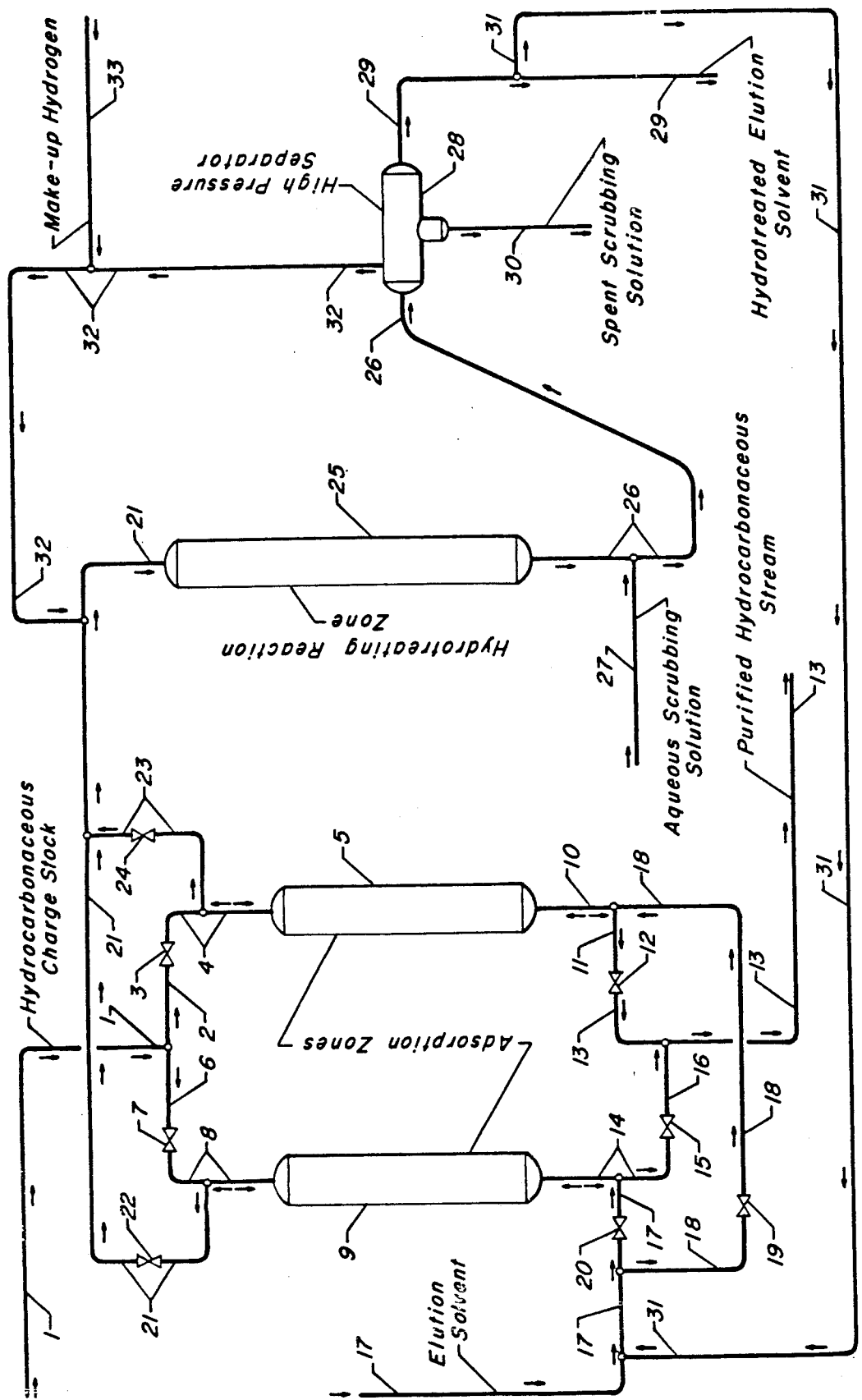

PROCESS FOR THE REMOVAL OF HYDROGENATABLE HYDROCARBONACEOUS COMPOUNDS FROM A HYDROCARBONACEOUS STREAM AND HYDROGENATING THESE COMPOUNDS

CROSS REFERENCE TO RELATED APPLICATION

This application is a continuation-in-part of application Ser. No. 930,624 filed Nov. 14, 1986, abandoned, all the teachings of which are hereby incorporated by reference.

BACKGROUND OF THE INVENTION

The field of art to which this invention pertains is the removal of hydrogenatable hydrocarbonaceous compounds from a hydrocarbonaceous stream. More particularly, the invention relates to the removal of hydrogenatable hydrocarbonaceous compounds which are hazardous or otherwise obnoxious. More specifically, the invention relates to a process for the removal of hydrogenatable hydrocarbonaceous compounds comprising a component selected from the group consisting of halogen, metal, sulfur, oxygen and nitrogen from a hydrocarbonaceous stream which comprises the steps of: (a) contacting the hydrocarbonaceous stream with an adsorbent to remove at least a portion of the hydrogenatable hydrocarbonaceous compounds from the hydrocarbonaceous stream to provide a hydrocarbonaceous stream having a reduced concentration of hydrogenatable hydrocarbonaceous compounds; (b) contacting spent adsorbent which has accumulated the hydrogenatable hydrocarbonaceous compounds from the hydrocarbonaceous stream with an elution solvent to remove the hydrogenatable hydrocarbonaceous compounds from the spent adsorbent thereby regenerating the adsorbent; (c) contacting the elution solvent in admixture with the hydrogenatable hydrocarbonaceous compounds which were removed from the spent adsorbent in step (b) in the presence of hydrogen with a hydrogenation catalyst in a hydrotreating reaction zone; (d) contacting the hydrotreating reaction zone effluent with an aqueous scrubbing solution; (e) introducing a resulting admixture of the reaction zone effluent and the aqueous scrubbing solution into a separation zone to provide a hydrotreated elution solvent and a spent aqueous stream; and (f) recycling at least a portion of the hydrotreated elution solvent from step (e) to provide at least a portion of the elution solvent utilized in step (b).

INFORMATION DISCLOSURE

In U.S. Patent No. 3,919,398 (Davis), a method is disclosed for the production and recovery of bromine as hydrogen bromide from aromatic bromides. The method involves reacting the aromatic bromide with hydrogen at a temperature within the range from about 200 to about 600° C. in the presence of a palladium activated catalyst. The '398 patent recovers the resulting hydrogen bromide as a product and does not contemplate the neutralization of the acid gas with an aqueous scrubbing solution. The '398 patent does not disclose that the aromatic bromide is eluted from a spent adsorbent with an elution solvent which is co-processed in a hydrotreating zone and the subsequent recycling of the hydrogenated elution solvent to regenerate additional spent adsorbent.

In U.S. Patent No. 3,892,818 (Scharfe et al.), a method is disclosed for the conversion of hydrocarbon chlorides in the presence of hydrogen to hydrocarbons and hydrogen chloride wherein the process takes place in a gaseous phase and in the presence of a rhodium-containing catalyst. The '818 patent does not teach or disclose the co-processing of a halogenated hydrocarbon and an elution solvent which has been used to regenerate a spent adsorbent containing the halogenated hydrocarbon, and the subsequent recycle of the hydrogenated elution solvent to regenerate additional spent adsorbent.

In U.S. Patent No. 4,201,665 (Savage et al.), a method is disclosed for the use of nonstoichiometric carbon-sulfur compounds to remove a wide variety of organic and/or inorganic materials from liquids. The '665 patent teaches that the removal of biorefractory organics, such as aromatics, is particularly effective and that the spent adsorbent may then be regenerated. The '665 patent also teaches that organic components subject to removal include, but are not limited to, aromatic compounds, aliphatic compounds, phenolic compounds, organic acids, alcohols, esters, aldehydes, amines, pyridines, morpholines, esters, glycols, glycol ethers, halogenated hydrocarbons, ketones, oxides, vinyl chloride and the like.

In U.S. Patent No. 3,595,931 (Hay et al.), a process is disclosed to replace the halogen moiety on a halogenated aromatic with hydrogen by contacting the halogenated aromatic in the vapor phase in the presence of hydrogen with a supported catalyst containing a minor amount of platinum or palladium and a minor amount of a hydrated alkali or alkaline earth metal oxide such as potassium hydroxide.

In Kirk-Othmer, *Encyclopedia of Chemical Technology*, Third Edition, Volume 12, at page 999, a method is described to remove hydrogen chloride by scrubbing a gaseous mixture with water. Kirk-Othmer does not teach the neutralization of an acid gas which is generated in a hydrotreating zone during the hydrogenation of a halogenated hydrocarbon.

In U.S. Patent No. 4,578,194 (Reinartz et al.), a process is disclosed for the removal of polychlorinated biphenyls (PCB) from transformer-insulating liquids using an adsorption resin. The insulating liquid is passed through the adsorption resin and after enrichment with PCB oil, the resin is washed with a solvent for PCB oils in order to regenerate the resin for reuse. A disadvantage of the '194 patent is that a solvent liquid contaminated with PCB is generated and must then be properly subjected to disposition. The '194 patent teaches that the solvent liquid contaminated with PCB may be regenerated by recovery of PCB by means of distillation which results in the continued existence of PCB compounds.

BRIEF SUMMARY OF THE INVENTION

The present invention provides a process for the removal of hydrogenatable hydrocarbonaceous compounds from a hydrocarbonaceous stream by contacting the hydrocarbonaceous stream with an adsorbent to remove at least a portion of the hydrogenatable hydrocarbonaceous compounds from the hydrocarbonaceous stream and whereby the spent adsorbent is regenerated by removal of accumulated hydrogenatable hydrocarbonaceous compounds from the adsorbent by means of an elution solvent and subsequent processing of the hydrogenatable hydrocarbonaceous compounds in a hydrotreating reaction zone to provide hydrogenated hydrocarbonaceous compounds and hydrotreated elution solvent. The present invention also contemplates the recycle of hydrotreated elution solvent to a spent adsorbent for removal of hydrogenatable hydrocarbonaceous compounds.

One embodiment of the invention may be characterized as a process for the removal of hydrogenatable hydrocarbonaceous compounds comprising a component selected from the group consisting of halogen, metal, sulfur, oxygen and nitrogen from a hydrocarbonaceous stream which comprises the steps of: (a) contacting the hydrocarbonaceous stream with an adsorbent to remove at least a portion of the hydrogenatable hydrocarbonaceous compounds from the hydrocarbonaceous stream to provide a hydrocarbonaceous stream having a reduced concentration of hydrogenatable hydrocarbonaceous compounds; (b) contacting spent adsorbent which has accumulated the hydrogenatable hydrocarbonaceous compounds from the hydrocarbonaceous stream with an elution solvent to remove the hydrogenatable hydrocarbonaceous compounds from the spent adsorbent thereby regenerating the adsorbent; (c) contacting the elution solvent in admixture with the hydrogenatable hydrocarbonaceous compounds which were removed from the spent adsorbent in step (b) in the presence of hydrogen with a hydrogenation catalyst in a hydrotreating reaction zone; (d) contacting the hydrotreating reaction zone effluent with an aqueous scrubbing solution; (e) introducing a resulting admixture of the reaction zone effluent and the aqueous scrubbing solution into a separation zone to provide a hydrotreated elution solvent and a spent aqueous stream; and (f) recycling at least a portion of the hydrotreated elution solvent from step (e) to provide at least a portion of the elution solvent utilized in step (b).

Other embodiments of the subject invention encompass further details such as potential hydrogenatable hydrocarbonaceous compounds, aqueous scrubbing solutions, hydrotreating catalysts, adsorbents, elution solvents and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

There is a steadily increasing demand for technology which is capable of eliminating hydrogenatable hydrocarbonaceous compounds from hydrocarbonaceous streams. In many instances, hydrogenatable hydrocarbonaceous compounds must be reduced or eliminated before a hydrocarbonaceous stream may be utilized or properly discarded. In the event that these hydrogenatable hydrocarbonaceous compounds are toxic, carcinogenic or otherwise obnoxious, it is preferred that the hydrogenatable hydrocarbonaceous compounds not only be removed from the hydrocarbonaceous stream but converted into less noxious compounds. Therefore, those skilled in the art have sought to find feasible techniques to remove hydrogenatable hydrocarbonaceous compounds from a hydrocarbonaceous stream and the subsequent conversion of the recovered hydrogenatable hydrocarbonaceous compounds.

It is well known that the art broadly teaches that organic compounds may be adsorbed from a hydrocarbonaceous stream by contacting the hydrocarbonaceous stream with an adsorbent and subsequently regenerating the spent adsorbent with an elution solvent. Furthermore, it is known that a halogenated aromatic compound may be hydrogenated in the presence of hydrogen and a hydrogenation or hydrotreating catalyst and that hydrogen chloride may be scrubbed from a gaseous admixture comprising hydrogen chloride with water. We have discovered an integrated process for the removal of hydrogenatable hydrocarbonaceous compounds from a hydrocarbonaceous stream by contacting the hydrocarbonaceous stream with an adsorbent to remove at least a portion of the hydrogenatable hydrocarbonaceous compounds from the hydrocarbonaceous stream and whereby the spent adsorbent is regenerated by the removal of accumulated hydrogenatable hydrocarbonaceous compounds from the adsorbent by means of an elution solvent and subsequent processing of the elution solvent in admixture with the desorbed hydrogenatable hydrocarbonaceous compounds in a hydrotreating reaction zone. At least a portion of the resulting hydrotreated elution solvent is recycled to provide at least a portion of the elution solvent used to regenerate spent adsorbent.

The present invention provides an improved and novel process for the removal of hydrogenatable hydrocarbonaceous compounds from a hydrocarbonaceous stream and the subsequent recovery and conversion thereof. A wide variety of hydrogenatable hydrocarbonaceous compounds are to be considered candidates for removal from a hydrocarbonaceous stream in accordance with the process of the present invention. Examples of hydrogenatable hydrocarbonaceous compounds which are suitable for treatment by the process of the present invention are halogenated hydrocarbons. Certain halogenated hydrocarbons having demonstrated or potential toxicity include but are not limited to kepone, halogenated biphenyls, halogenated cyclodienes, such as aldrin, dieldrin, and hexachlorocyclopentadienes, dibromochloropropane, halogenated phthalic anhydrides, such as polybromophthalicanhydride, tetrachloroethylene, tetrachloroethane, polychlorodioxins such as tetrachlorodibenzodioxin, halogenated organic phosphates such as 2,2 dichlorovinyldimethyl phosphate. Additional examples of hydrogenatable hydrocarbonaceous compounds which are suitable for treatment include organometallic compounds and especially those which contain metals such as lead, mercury, cadmium, cobalt, arsenic, vanadium, and chromium. Polynuclear aromatic compounds are also contemplated as hydrogenatable hydrocarbonaceous compounds. Hydrogenatable hydrocarbonaceous compounds may comprise sulfur, oxygen, metal or nitrogen components. In accordance with the present invention, generally any hydrogenatable hydrocarbonaceous compound may be removed from a hydrocarbonaceous stream. It is preferred that the hydrogenatable hydrocarbonaceous compounds are present in the hydrocarbonaceous stream in an amount less than about 30 weight percent and more preferably less than about 10,000 PPM by weight and most preferably in an amount less than about 5,000 PPM by weight.

In accordance with the subject invention, a hydrocarbonaceous stream containing hydrogenatable hydrocarbonaceous compounds comprising a component selected from the group consisting of halogen, metal, sulfur, oxygen and nitrogen is contacted with a suitable adsorbent which selectively retains the hydrogenatable hydrocarbonaceous compounds and produces a hydrocarbonaceous stream with a reduced concentration of hydrogenatable hydrocarbonaceous compounds. Suitable adsorbents may be selected from materials which exhibit the primary requirement of hydrogenatable hydrocarbonaceous compound selectivity and which are otherwise convenient to use. Suitable adsorbents include, for example, molecular sieves, adsorption resin, amorphous silica-alumina gel, silica gel, activated carbon, activated alumina and clays. Of course, it is recognized that for a given case, a particular adsorbent may give better results than others.

In the case where polychlorinated biphenyls (PCB) are present in a hydrocarbonaceous stream, a suitable PCB adsorbent for use in accordance with the present invention is taught in U.S. Patent No. 4,578,194 (Reinartz et al). A preferred adsorbent of the '194 patent is a polymeric adsorption resin such as, for example, an insoluble cross-linked polystyrene resin which is readily commercially available.

The selected adsorbent is contacted with a hydrocarbonaceous stream containing hydrogenatable hydrocarbonaceous compounds in an adsorption zone. The adsorbent may be installed in the adsorption zone in any suitable manner. A preferred method for the installation of the adsorbent is in a fixed bed arrangement. The adsorbent may be installed in one or more vessels and in either series or parallel flow. The flow of a hydrocarbonaceous stream through the adsorption zone is preferably performed in a parallel manner so that when one of the adsorbent beds or chambers is spent by the accumulation of hydrogenatable hydrocarbonaceous compounds thereon, the spent adsorbent zone may be bypassed while continuing uninterrupted operation through the parallel adsorbent zone.

During adsorption, the adsorption zone is preferably maintained at a pressure from about atmospheric to about 1500 psig (10342 k Pa gauge), a temperature from about 32° F. (0° C.) to about 300° F. (149° C.) and a liquid hourly space velocity from about 0.1 $hr^{-1}$ to about 500 $hr^{-1}$. The flow of the hydrocarbonaceous stream containing hydrogenatable hydrocarbonaceous compounds through the adsorption zone may be conducted in an upflow, downflow or radial flow manner. The temperature and pressure of the adsorption zone are preferably selected to maintain the hydrocarbonaceous stream in the liquid phase. As used herein, the term "essentially hydrogenatable hydrocarbon-free" connotes a hydrogenatable hydrocarbonaceous compound concentration of less than about 10 PPM.

The spent zone of adsorbent is regenerated by isolating the spent adsorption zone and contacting the adsorbent with an elution solvent to remove the hydrogenatable hydrocarbonaceous compounds thereby regenerating the adsorbent. In general, an elution solvent is utilized which possesses a high solvent selectivity towards the hydrogenatable hydrocarbonaceous compounds adsorbed on the adsorbent and which has no deleterious effect on the adsorbent. Preferred elution solvents comprise naphtha, kerosene, diesel fuel, gas oil or mixtures thereof. Additional elution solvents which are contemplated for use in the present invention include acetone, methylethylketone, or any other convenient organic solvent. It is recognized that when certain elution solvents are hydrotreated the elution solvents may undergo conversion to reaction products which are deemed less suitable for recycle as an elution solvent than the virgin elution solvent. During regeneration of the adsorbent, the adsorption zone is preferably maintained at a pressure from about atmospheric to about 1500 psig (10342 k Pa gauge), and a temperature from about 32° F. (0° C.) to about 700° F. (371° C.). The flow of the elution solvent through the adsorption zone during regeneration thereof may be conducted in an upflow, downflow or radial flow manner. The elution solvent during the regeneration of adsorbent may be present in a liquid phase or a gasliquid mixed phase.

The resulting elution solvent containing the hydrogenatable hydrocarbonaceous compounds is introduced into a hydrotreating or hydrogenation zone and is contacted with a hydrogen-rich gaseous phase and a hydrogenation catalyst in order to hydrogenate at least a portion of the hydrogenatable hydrocarbonaceous compounds. The catalytic hydrogenation zone may contain a fixed, ebulated or fluidized catalyst bed. This reaction zone is preferably maintained under an imposed pressure from about 100 psig (689 k Pa gauge) to about 2000 psig (13790 k Pa gauge) and more preferably under a pressure from about 200 psig (1379 k Pa gauge) to about 1800 psig (12411 k Pa gauge). Suitably, such reaction is conducted with a maximum catalyst bed temperature in the range of about 350° F. (177° C.) to about 850° F. (454° C.) selected to perform the desired hydrotreating conversion to reduce, or eliminate, the concentration of hydrogenatable hydrocarbonaceous compounds. Further preferred operating conditions include liquid hourly space velocities in the range from about 0.2 $hr^{-1}$ to about 10 $hr^{-1}$ and hydrogen circulation rates from about 200 standard cubic feet per barrel (SCFB) (35.6 $m^3/m^3$) to about 10,000 SCFB (1778 $m^3/m^3$), preferably from about 300 SCFB (53.3 $m^3/m^3$) to about 8000 SCFB (1422 $m^3/m^3$).

A preferred catalytic composite disposed within the hereinabove described hydrogenation zone can be characterized as containing a metallic component having hydrogenation activity, which component is combined with a suitable refractory inorganic oxide carrier material of either synthetic or natural origin. The precise composition and method of manufacturing the carrier material is not considered essential to the present invention. Preferred carrier materials are alumina, silica and mixtures thereof. Suitable metallic components having hydrogenation activity are those selected from the group comprising the metals of Groups VI-B and VIII of the Periodic Table, as set forth in the Periodic Table of the Elements, E. H. Sargent and Company, 1964. Thus, the catalytic composites may comprise one or more metallic components from the group of molybdenum, tungsten, chromium, iron, cobalt, nickel, platinum, iridium, osmium, rhodium, ruthenium, and mixtures thereof. The concentration of the catalytically active metallic component, or components, is primarily dependent upon a particular metal as well as the physical and/or chemical characteristics of the particular hydrocarbon feedstock. For example, the metallic components of Group VI-B are generally present in an amount within the range of from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. In addition, any catalyst employed commercially for hydrotreating middle distillate hydrocarbonaceous compounds to remove nitrogen and sulfur should normally function effectively in the hydrogenation zone of the present invention. In the event that the hydrogenatable hydrocarbonaceous compounds contain relatively high concentrations of halogen, a preferred catalyst would comprise a carbon support or carrier material which would be capable of displaying more resistance to dissolution and subsequent degradation than would an inorganic oxide carrier material.

The hydrocarbonaceous effluent from the hydrogenation zone is contacted with an aqueous scrubbing solution and the resulting admixture is admitted to a separation zone in order to separate a spent aqueous scrubbing solution, a hydrogenated hydrocarbonaceous phase comprising hydrotreated elution solvent and hydrotreated hydrocarbonaceous compounds which formerly were identified as hydrogenatable hydrocarbonaceous compounds and a hydrogen-rich gaseous phase. The contact of the hydrocarbonaceous effluent from the hydrogenation zone with the aqueous scrubbing solution may be performed in any convenient manner and is preferably conducted by cocurrent, in-line mixing which may be promoted by inherent turbulence, mixing orifices or any other suitable mixing means. The aqueous scrubbing solution is preferably introduced in an amount from about 1 to about 40 volume percent based on the hydrocarbonaceous effluent from the hydrogenation zone. The aqueous scrubbing solution is selected depending on the characteristics of the hydrogenatable hydrocarbonaceous compounds which are removed from the hydrocarbonaceous charge stock. For example, if the hydrogenatable hydrocarbonaceous compounds present in the hydrogenaceous charge stock comprise halogenated compounds, the aqueous scrubbing solution preferably contains a basic compound such as calcium hydroxide, potassium hydroxide or sodium hydroxide in order to neutralize the acid which is formed during the hydrogenation of the hydrocarbonaceous halogen compounds. In the event that the hydrogenatable hydrocarbonaceous compounds contain only sulfur and nitrogen compounds, pure water is a suitable aqueous scrubbing solution. The resulting hydrotreated hydrocarbonaceous phase is recovered and the hydrogen-rich gaseous phase may be recycled to the hydrogenation zone if desired. In accordance with the subject invention, at least a portion of the recovered hydrocarbonaceous phase is recycled as at least a portion of the elution solvent mentioned hereinabove. A portion of the aqueous scrubbing solution recovered in the separation zone may be recycled to contact the hydrocarbonaceous effluent from the hydrogenation zone. The spent aqueous scrubbing solution may be neutralized or otherwise treated to provide a more environmentally acceptable effluent.

In the drawing, the process of the present invention is illustrated by means of a simplified flow diagram in which such details as pumps, instrumentation, heat-exchange and heat-recovery circuits, compressors, surge tanks and similar hardware have been deleted as being non-essential to an understanding of the techniques involved. The use of such miscellaneous appurtenances are well within the purview of one skilled in the art.

With reference now to the drawing, a hydrocarbonaceous charge stock containing hydrogenatable hydrocarbonaceous compounds is introduced into the process via conduit 1 and is passed via conduit 2, valve 3 and conduit 4 into adsorption zone 5. Alternatively, the hydrocarbonaceous charge stock is introduced via conduit 6, valve 7, and conduit 8 into adsorption zone 9 which is located in parallel with adsorption zone 5. A hydrocarbonaceous stream having a reduced concentration of hydrogenatable hydrocarbonaceous compounds is removed from adsorption zone 5 via conduit 10, conduit 11, valve 12, conduit 13 and recovered. In the alternative, a hydrocarbonaceous stream having a reduced concentration of hydrogenatable hydrocarbonaceous compounds is removed from adsorption zone 9 via conduit 14, valve 15, conduit 16, conduit 13 and recovered. In the event adsorption zone 9 is to be regenerated, valves 7 and 15 are closed for isolation and an elution solvent is introduced via conduit 17, valve 20, conduit 17, and conduit 14 into adsorption zone 9. An elution solvent rich in hydrogenatable hydrocarbonaceous compounds which have been extracted from adsorption zone 9 is removed via conduit 8, conduit 21, valve 22 and conduit 21 and is introduced into hydrotreating reaction zone 25. In the event that adsorption zone 5 is to be regenerated, valves 3 and 12 are closed for isolation and an elution solvent is introduced via conduit 17, conduit 18, valve 19, conduit 18 and conduit 10 into adsorption zone 5. An elution solvent rich in hydrogenatable hydrocarbonaceous compounds is removed from adsorption zone 5 via conduit 4, conduit 23, valve 24, conduit 23, and conduit 21 and introduced into hydrotreating reaction zone 25. A hydrogen-rich gaseous stream which is derived in a manner hereinafter described is introduced via conduit 32 and conduit 21 into hydrotreating reaction zone 25. Make-up hydrogen is introduced via conduit 33, conduit 32 and conduit 21 into hydrotreating reaction zone 25. The admixture of elution solvent and hydrogenatable hydrocarbonaceous compounds is hydrogenated in hydrotreating reaction zone 25 in the presence of a hydrogenation catalyst: maintained at hydrogenation conditions as described hereinabove. The resulting hydrotreated elution solvent and hydrocarbonaceous compounds and a gaseous phase are removed from hydrotreating reaction zone 25 via conduit 26 and contacted with an aqueous scrubbing solution introduced via conduit 27. The resulting mixture is introduced via conduit 26 into high pressure separator 28. A hydrogen-rich gaseous phase is removed from high pressure separator 28 via conduit 32 and recycled as described hereinabove. A hydrocarbonaceous stream comprising hydrotreated elution solvent is removed from high pressure separator 28 via conduit 29 and recovered. At least a portion of the hydrocarbonaceous stream comprising hydrotreated elution solvent is recycled via conduit 31 to provide at least a portion of the elution solvent which is provided via conduit 17. A spent aqueous scrubbing solution is removed from high pressure separator 28 via conduit 30 and is recovered.

The process of the present invention is further demonstrated by the following illustrative embodiment. This illustrative embodiment is however not presented to unduly limit the process of this invention, but to further illustrate the advantages of the hereinabove described embodiments. The following data were not obtained by the actual performance of the present invention, but are considered prospective and reasonably illustrative of the expected performance of the invention.

ILLUSTRATIVE EMBODIMENT

This illustrative embodiment describes the removal of polychlorinated biphenyl (PCB) from a hydrocarbonaceous stream which contains 500 weight PPM of PCB in an adsorption zone, the subsequent elution of the PCB from an adsorbent contained in the adsorption zone and the conversion of the eluted PCB by hydrotreating to produce innocuous hydrocarbonaceous compounds.

A hydrocarbonaceous stream containing 500 weight PPM of PCB is introduced into an adsorption zone containing cross-linked polystyrene resin particles at conditions including a temperature of about 100° F. (38° C.), a pressure of about 10 psig (69 k Pa gauge), and a liquid hourly space velocity of about 10. The resulting hydrocarbonaceous stream is found to contain less than 1 PPM of PCB. Another adsorption zone containing crosslinked polystyrene resin particles which is located in parallel with the hereinabove mentioned adsorption zone and is regenerated to remove previously adsorbed PCB by contacting the resin particles containing PCB with an elution solvent comprising naphtha which is at least partially derived from the hydrotreated elution solvent hereinafter described at conditions which include a temperature of about 250° F. (121° C.), and a pressure of about 10 psig (69 k Pa gauge) for a time sufficient to elute or remove substantially all of the transient PCB from the resin adsorbent. The resulting admixture of elution solvent and PCB removed from the adsorbent is then introduced together with a gaseous hydrogen-rich stream into a hydrotreating reaction zone loaded with a catalyst comprising alumina, cobalt and molybdenum. The hydrotreating reaction is conducted with a catalyst peak temperature of 750° F. (399° C.), a pressure of 900 psig (6205 k Pa gauge), a liquid hourly space velocity of 1 based on fresh feed and a hydrogen circulation rate of 2500 SCFB (444 std m$^3$/m$^3$). The effluent from the hydrotreating reaction zone is contacted with an aqueous sodium hydroxide solution in an amount of 10 volume percent based on the hydrocarbonaceous effluent from the hydrotreating zone. The admixture of the hydrotreating reaction zone effluent and the aqueous scrubbing solution is introduced into a separation zone to provide a spent aqueous stream and a hydrotreated elution solvent having less than 1 PPM of PCB.

The foregoing description, drawing and illustrative embodiment clearly illustrate the advantages encompassed by the process of the present invention and the benefits to be afforded with the use thereof.

We claim as our invention:

1. A process for the removal of hydrogenatable hydrocarbonaceous compounds comprising a component selected from the group consisting of halogen, metal, sulfur, oxygen and nitrogen from a hydrocarbonaceous stream which comprises the steps of:
   (a) contacting said hydrocarbonaceous stream with an adsorbent to remove at least a portion of said hydrogenatable hydrocarbonaceous compounds from said hydrocarbonaceous stream to provide a hydrocabonaceous stream having a reduced concentration of hydrogenatable hydrocarbonaceous compounds;
   (b) contacting spent adsorbent which has accumulated said hydrogenatable hydrocarbonaceous compounds from said hydrocarbonaceous stream with an elution solvent to remove said hydrogenatable hydrocarbonaceous compounds from said spent adsorbent thereby regenerating said absorbent;
   (c) contacting said elution solvent in admixture with said hydrogenatable hydrocarbonaceous compounds which were removed from said spent adsorbent in step (b) in the presence of hydrogen with hydrogenation catalyst in a hydrotreating reaction zone;
   (d) contacting hydrotreating reaction zone effluent with an aqueous scrubbing solution;
   (e) introducing a resulting admixture of said reaction zone effluent and said aqueous scrubbing solution into a separation zone to provide a hydrotreated elution solvent and a spent aqueous stream; and
   (f) recycling at least a portion of said hydrotreated elution solvent from step (e) to provide at least a portion of said elution solvent utilized in step (b).

2. The process of claim 1 wherein said hydrogenatable hydrocarbonaceous compounds comprise hazardous hydrocarbonaceous compounds.

3. The process of claim 1 wherein said hydrotreating reaction zone is operated at conditions which include a pressure from about 100 psig (689 k Pa gauge) to about 2000 psig (13790 k Pa gauge), a maximum catalyst temperature from about 350° F. (177° C.) to about 850° F. (454° C.) and a hydrogen circulation rate from about 200 SCFB (35.6 std m$^3$/m$^3$) to about 10,000 SCFB (1778 std m$^3$/m$^3$).

4. The process of claim 1 wherein said hydrogenation catalyst comprises a refractory inorganic oxide and at least one metallic compound having hydrogenation activity.

5. The process of claim 4 wherein said metallic compound is selected from the metals of Groups VI-B and VIII of the Periodic Table.

6. The process of claim 1 wherein said aqueous scrubbing solution comprises an alkaline compound.

7. The process of claim 6 wherein said alkaline compound is sodium hydroxide, potassium hydroxide or calcium hydroxide.

8. The process of claim 1 wherein said adsorbent is silica gel, activated carbon, activated alumina, silica-alumina gel, clay, molecular sieves, adsorption resin or admixtures thereof.

9. The process of claim 1 wherein said contacting conducted in step (a) is performed at conditions which include a pressure from about atmospheric to about 1500 psig (10342 k Pa gauge) and a temperature from about 32° F. (0° C.) to about 300° F. (149° C.) and a liquid hourly space velocity from about 0.1 hr$^{-1}$ to about 500 hr$^{-1}$.

10. The process of claim 1 wherein the adsorbent regeneration conducted in step (b) is performed at conditions which include a pressure from about atmospheric to about 1500 psig (10342 k Pa gauge) and a temperature from about 32° F. (0° C.) to about 700° F. (371° C.).

11. The process of claim 1 wherein said hydrocarbonaceous stream having a reduced hydrogenatable hydrocarbonaceous compound concentration is essentially free of hydrogenatable hydrocarbonaceous compounds.

12. The process of claim 1 wherein said elution solvent is naphtha, kerosene, diesel fuel, gas oil or mixtures thereof.

13. The process of claim 1 wherein said elution solvent is acetone or methylethylketone.

14. The process of claim 1 wherein said hydrogenatable hydrocarbonaceous compounds are present in said hydrocarbonaceous stream in an amount less than about 10,000 PPM by weight.

* * * * *